United States Patent [19]
Davis et al.

[11] Patent Number: 5,741,313
[45] Date of Patent: Apr. 21, 1998

[54] IMPLANTABLE MEDICAL DEVICE WITH A REDUCED VOLUMETRIC CONFIGURATION AND IMPROVED SHOCK STABILIZATION

[75] Inventors: Dion Frank Davis, Palmdale; Buehl E. Truex, Glendora; Clyde K. Nason, Valencia; William H. Stutz, Jr., Eagle Rock, all of Calif.

[73] Assignee: Pacesetter, Inc., Sylmar, Calif.

[21] Appl. No.: 711,012

[22] Filed: Sep. 9, 1996

[51] Int. Cl.$^6$ .................................................. A61N 1/375
[52] U.S. Cl. ............................................................. 607/36
[58] Field of Search ........................................ 607/36, 37

[56] References Cited

U.S. PATENT DOCUMENTS

| | | | |
|---|---|---|---|
| 3,866,616 | 2/1975 | Purdy et al. | 607/36 |
| 3,888,260 | 6/1975 | Fischell | 607/36 |
| 4,041,955 | 8/1977 | Kelley et al. | 607/36 |
| 4,254,775 | 3/1981 | Langer | 607/36 |
| 4,314,562 | 2/1982 | Ware | 607/36 |
| 5,040,534 | 8/1991 | Mann et al. | |
| 5,405,363 | 4/1995 | Kroll et al. | 607/5 |

Primary Examiner—William E. Kamm
Assistant Examiner—George R. Evanisko

[57] ABSTRACT

A cardiac stimulation device having a reduced volumetric configuration contains a pair of high-voltage cylindrical discharge capacitors positioned at rounded edges within a device container. The capacitors have electrical contact tabs at one end which are inserted directly through apertures formed within an associated electronic module. The capacitor tabs are connected directly to the electronic module eliminating the need for secondary connectors or point to point wiring, thus reducing the number of connections. Direct connection of the capacitors to the electronic module allows for optimal positioning of the module within the container. Specifically, the generally planar module is oriented perpendicular to planar cover surfaces of the container. Irregularly shaped components attached to the surface of the module advantageously extend away from the surface into remaining voids within the container. Adhesive compressible foam is placed around and between the internal components of the stimulation device to stabilize the device against shock and vibration.

34 Claims, 4 Drawing Sheets

Fig. 1

IMPLANTABLE MEDICAL DEVICE WITH A REDUCED VOLUMETRIC CONFIGURATION AND IMPROVED SHOCK STABILIZATION

FIELD OF THE INVENTION

This invention relates generally to implantable, cardiac stimulation devices. More particularly, this invention relates to methods and apparatus for configuring internal components of cardiac stimulation devices to reduce their overall volumetric displacement and improve their resistance to shock and vibration.

BACKGROUND OF THE INVENTION

Implantable cardiac stimulation devices include pacemakers, cardioverter-defibrillators, tachycardia therapy units, and other devices. It has been a primary goal among designers of implantable cardiac stimulation devices to reduce the overall size of these devices. Reducing the size of implantable medical devices benefits patients receiving the devices and leads to improved procedures for implanting the devices. With the advent of pectorally implantable therapy devices, such as tachycardia therapy devices, minimal volume has become a necessity to permit effective subcutaneous implantation. However, as cardiac stimulation devices become more technologically complex, the challenge of minimizing their overall size has become increasingly difficult.

The size of an implantable medical device is commonly measured in terms of volume, i.e., displacement, of the outer device case which holds the internal components. The volume of an implantable device is determined largely by the size and arrangement of the major components mounted within an exterior housing. For example, major components of cardioverter-defibrillator devices include the battery, storage capacitors, and electronics modules. In addition to the individual major components, the volume contribution from the interconnection architecture among these components can be appreciable.

There have been efforts within the implantable medical device field to reduce the size of the internal device components. However, because essential performance parameters of implantable devices must be maintained (such as the electrical charge energy and the physiologically effective current of a stimulation unit), certain major components can only be reduced in size by a limited amount in accordance with the most recent technological advances.

For example, in U.S. Pat. No. 5,405,363 (Kroll et al.), an implantable cardioverter-defibrillator (ICD) is disclosed which optimizes certain performance parameters to achieve a reduction in the size of the capacitors and battery. As a result, according to Kroll et al., an ICD displacement volume of less than 90 cc can be obtained allowing for pectoral implantation. Although advances, like that disclosed in Kroll et al., have been made in reducing the size of internal components placed within implantable devices, the resulting device volume decrease from this alone has not proven satisfactory to the medical community. Further advances which contribute to an overall reduction in device volume are desired to achieve comfortable pectoral implantability.

For a given implantable medical device design, consideration must be given to the movement of the internal components within the device container. This is especially true for implantable medical devices having components arranged in close proximity. Thus, internal components of implantable devices typically require some method of support and stabilization to ensure that the components are protected from sudden physical shocks or vibrations. Existing implantable devices may use skeletal plastic structures with pocket recesses for receiving the internal components. While skeletal support structures serve to protect against shock and vibration of an implantable device, there are limitations from their use. For example, skeletal support structures must be specially tooled adding to their initial cost and development cycle. Accordingly, a component design change after such tooling is complete can result in product delays and further retooling costs.

While advances have been made in reducing the size of implantable medical devices, it is recognized that further reductions are advantageous to both patients and the medical community. Also, the methods used to stabilize internal components of implantable devices have proven to be relatively expensive and time consuming to implement. Therefore, there is a need in the art for an improved implantable medical device which provides for a reduction in overall volume displacement from that of current devices. There is also a need in the art for an improved implantable medical device which provides a higher degree of internal component support and stabilization.

SUMMARY OF THE INVENTION

In accordance with a preferred embodiment of the present invention, an implantable cardiac stimulation device, such as a cardioverter-defibrillator, tachycardia therapy device or the like, has internal components uniquely configured to provide for a high degree of compactness. The stimulation device of the present invention has an outer container which typically has a generally rectangular cross section. The container is a two-piece unit with each piece having a flat cover surface terminating at a periphery. The periphery of the container, however, has rounded edges to provide an organically-shaped device which minimizes body compatibility issues.

For discussion purposes, a cardioverter-defibrillator is shown and described as the implantable medical device in accordance with a preferred embodiment. The internal components of the cardioverter-defibrillator include, among other items, a battery which may be cubically-shaped, cylindrically-shaped capacitors, electronics modules having a rectangurally shaped substrate for mounting electronic components thereon. The electronics modules include a high-voltage module for delivering an electric pulse to a patient, and a low-voltage electronics module for controlling the operation of the implantable device.

The organic, or rounded, edges of the device container inevitably results in rounded voids near the periphery of the container. Specifically, along the four edges of the implantable device, longitudinal sections of semi-circular cross section exist within the device container. The present invention optimizes the placement and configuration of the internal device components, and their interconnection, to take advantage of the organically-shaped container.

In accordance with a preferred embodiment of an implantable medical device, cylindrical capacitors, which typically have flat top and bottom surfaces, are located near the periphery of the device container. The capacitors are physically positioned in parallel at opposite ends to neatly fit within two of the rounded voids of the container. A cubical battery is placed between the capacitors near the center of the device container. The remaining sections within the device container consist largely of two remaining rounded peripheral sections residing at the top and bottom portions of the capacitors, respectively.

To achieve an increased volumetric efficiency, the electronics modules of the implantable medical device are located within the two rounded sections of the container near the top and bottom portions of the capacitors. The electronics modules are advantageously mounted so that the planar axis of the modules lie perpendicular to the flat cover surfaces of the device container. The high-voltage module is placed at one end of the capacitors and connected thereto, while the other module is placed at an opposite end of the capacitors.

In addition, the high-voltage module is positioned so that the electrical tabs of the capacitors are inserted directly through slots formed in the substrate of the high-voltage module. This simplified interconnection architecture eliminates bulky flexible circuits or additional point-to-point wiring that otherwise adds to the volume of the device and the number of electrical connections required.

To guard against shock and vibration of the implantable medical device, a support structure may be used to configure the internal components within the device container. In one embodiment, double-sided adhesive foam tape, which is slightly compressible, is used as a support structure and placed between respective internal components and/or between a given component and the device container. This results in a rigid device structure which provides a greater degree of shock damping from that found in the prior art.

Accordingly, in accordance with a preferred embodiment, a high density of components is achieved within an implantable medical device leading to a reduced volumetric displacement. Also in accordance with a preferred embodiment, structural stabilization of the internal components is achieved through a unique and relatively simplistic method of applying compressible foam adhesive tape to the components and the device container.

BRIEF DESCRIPTION OF THE DRAWINGS

The above and other aspects, features and advantages of the present invention will be more apparent from the following particular descriptions thereof presented in conjunction with the following drawings wherein.

DETAILED DESCRIPTION OF THE PREFERRED EMBODIMENT

Figure 1:
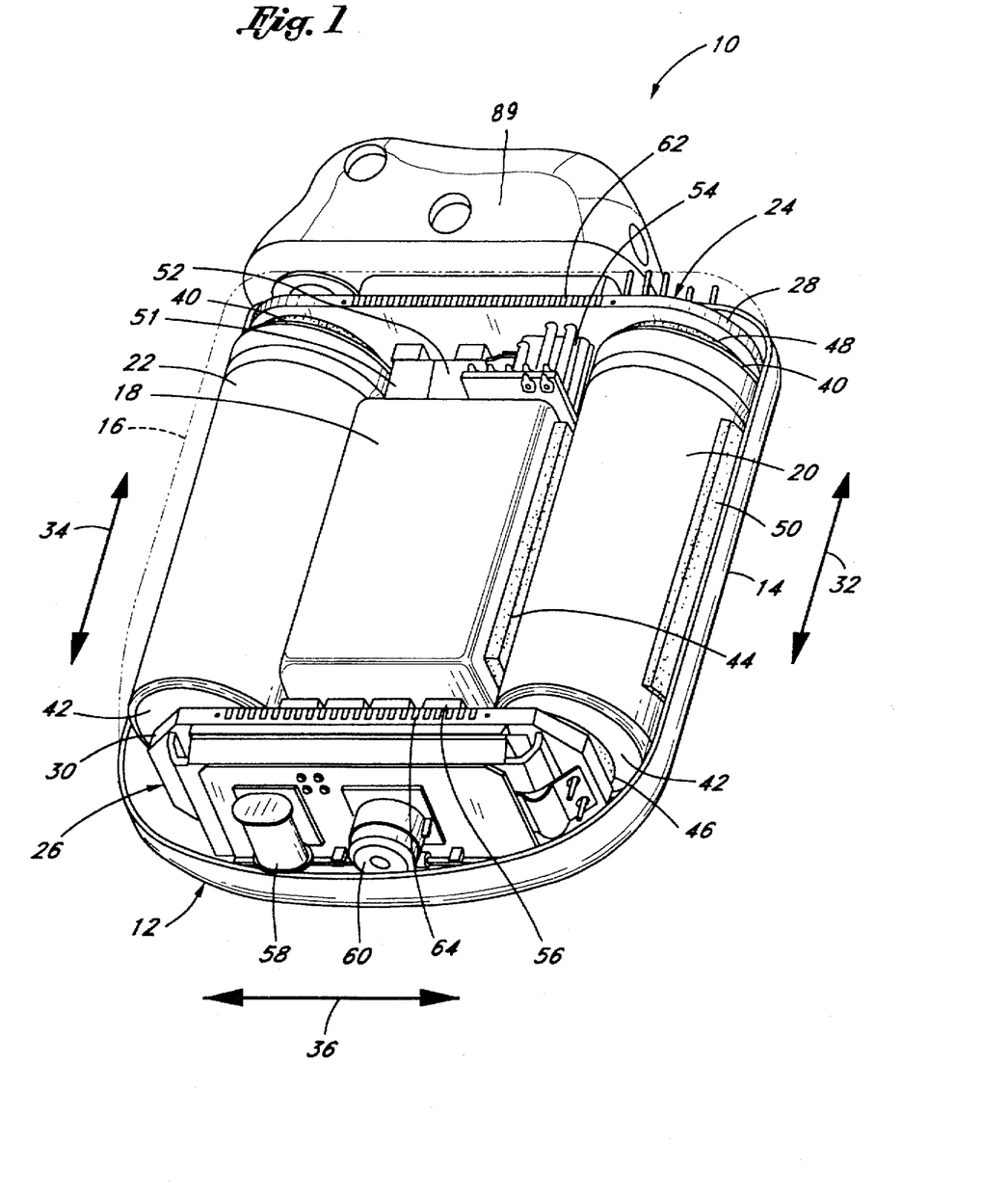
FIG. 1 is a perspective view depicting the configuration of the internal components of a cardiac stimulation device in accordance with a preferred embodiment.

Referring initially to FIG. 1, an implantable cardiac stimulation device 10 is shown in accordance with a preferred embodiment. The device 10, which may be a cardioverter-defibrillator, as shown in FIG. 1, or other stimulation device, has an exterior two-piece container 12 constructed of a biocompatible material. The container 12 comprises a bottom container portion 14 and a top container portion 16 (shown in phantom). Housed within the container 12 are internal components including a battery 18, charge capacitors 20 and 22, a high-voltage electronics module 24, and a low voltage electronics module 26.

Each of the electronics modules 24 and 26 is a hybrid circuit module which may contain multi-level circuit structures. The modules 24 and 26 also contain a generally rectangular and planar substrate 28 and 30, respectively. The substrate may be constructed of a ceramic material or other material common to one of ordinary skill in the art. Mounted upon each of the substantially planar substrates 28 and 30, are individual electronic components such as integrated circuit devices or passive circuit elements. The high voltage discharge module 24 operates to deliver a high-voltage pulse to a patient, typically on the order of 500–750 volts. Before a high-voltage discharge occurs, the battery 18 first charges a discharge capacitor assembly comprising the capacitors 20 and 22. In response to a cardiac arrhythmia of a host patient, the capacitors 20 and 22 are discharged through the high voltage module 24. The electric discharge is transferred to the heart of a patient via stimulus leads (not shown) connected to the connector top 89.

The low voltage module 26 is a control module which performs cardiac pacing and sensing functions for determining when a high voltage discharge is warranted. The basic design and operation of a typical cardioverter-defibrillator, including the basic operational aspects performed by the modules 24 and 26, are common to one of ordinary skill in the art and will not be discussed in detail in accordance with a preferred embodiment of the present invention. Such details can be found in U.S. Pat. No. 5,405,363 (Kroll et al.) and U.S. Pat. No. 5,040,534 (Mann et al.), both of which are incorporated herein by reference as though fully set forth.

The internal components of the device 10, including the battery 18, the capacitors 20 and 22, and the modules 24 and 26, are uniquely configured within the container 12 to optimize available space. As can be seen in FIG. 1, the container 12 has a generally rectangular cross section with rounded edges to create organically shaped contours that minimize body compatibility issues arising from implantation. The rounded periphery of the container 12 creates substantially semi-circular internal portions, i.e., rounded voids, within the container 12. These rounded voids are formed along the container periphery at side edges denoted by lines 32 and 34, along a top edge adjacent to the module 24, and also along a bottom edge denoted by a line 36. Internal components of the device 10 are advantageously placed within these substantially semi-circular internal portions of the container 12.

Specifically, the capacitors 20 and 22 are placed at opposite sides within the container 12 so that the longitudinal axes of the capacitors are parallel with the side edges of the container referenced by the lines 32 and 34. This allows the cylindrical shape of the capacitors 20 and 22 to fit optimally within the container 12. The battery 18 fits between the capacitors 20 and 22 near the center of the container 12. The battery 18 is typically cubical in shape to achieve acceptable electrical efficiency. Although a cubically-shaped battery is shown in FIG. 1, it can be appreciated by one of ordinary skill that batteries of different shapes may be placed within the container without departing from the spirit of the invention.

Because the cylindrical capacitors 20 and 22 have flat top surfaces 40, flat bottom surfaces 42, and the container 12 has rounded edges, the capacitors 20 and 22 are ideally centered along their longitudinal axes within the container 12. This configuration of the capacitors leaves empty space within the container near the top and bottom capacitor surfaces 40 and 42. The empty space which is left can be described as longitudinal areas of semi-circular cross-section located perpendicular to the central axes of the capacitors. To achieve maximum volumetric efficiency, the modules 24 and 26 are fitted at the top and bottom capacitor surfaces 40 and 42, respectively, to fill much of the remaining container area. Also shown in FIG. 1 are adhesive foam elements 44, 46, 48, and 50, which are attached to individual components to guard against shock and vibration as will be more fully discussed in connection with FIGS. 2 and 5.

In accordance with a preferred embodiment, each of the modules 24 and 26 is positioned so that the substantially planar surface of the substrates 28 and 30, respectively, is perpendicular to the large planar covering surfaces of the container 12. The modules 24 and 26 communicate through electrical contacts 62 and 64, respectively, via a flex circuit connector (not shown). The module 24 is positioned above the top surfaces 40 of the capacitors 20 and 22 while the module 26 is positioned below the bottom surfaces 42. In this configuration, circuit elements attached to the modules 24 and 26 are advantageously positioned to extend into unfilled space within the container. Thus, volumetric efficiency of the container 12 is enhanced through careful positioning of the internal components to take advantage of all usable space.

In particular, as shown in FIG. 1, circuit elements 51, 52, and 54, which are mounted to the substrate 28, extend inwardly towards the center of the container 12 and the battery 18. Likewise, a component package 56 of the module 26 is mounted to the substrate 30 and extends inwardly towards the battery 18 from an opposite edge of the container 12. The module 26 also has additional circuit components 58 and 60 which extend outwardly toward the edge (represented by the line 36) of the container 12. The perpendicular positioning of the substrates 28 and 30 with the planar surfaces of the container 12 allows for the optimal positioning of these internal components. Specifically, irregularly-shaped circuit elements, such as the components 51, 52, 54, 56, 58, and 60 are advantageously placed within the peripheral voids of the container 12.

For ease of explanation, only certain circuit components of the modules 24 and 26 have been shown and described in accordance with a preferred embodiment. It can be appreciated by one of ordinary skill in the art that the positioning of the modules 24 and 26 as shown in FIG. 1 allows a variety of attached circuit components to be optimally placed within the described container voids.

Figure 2:
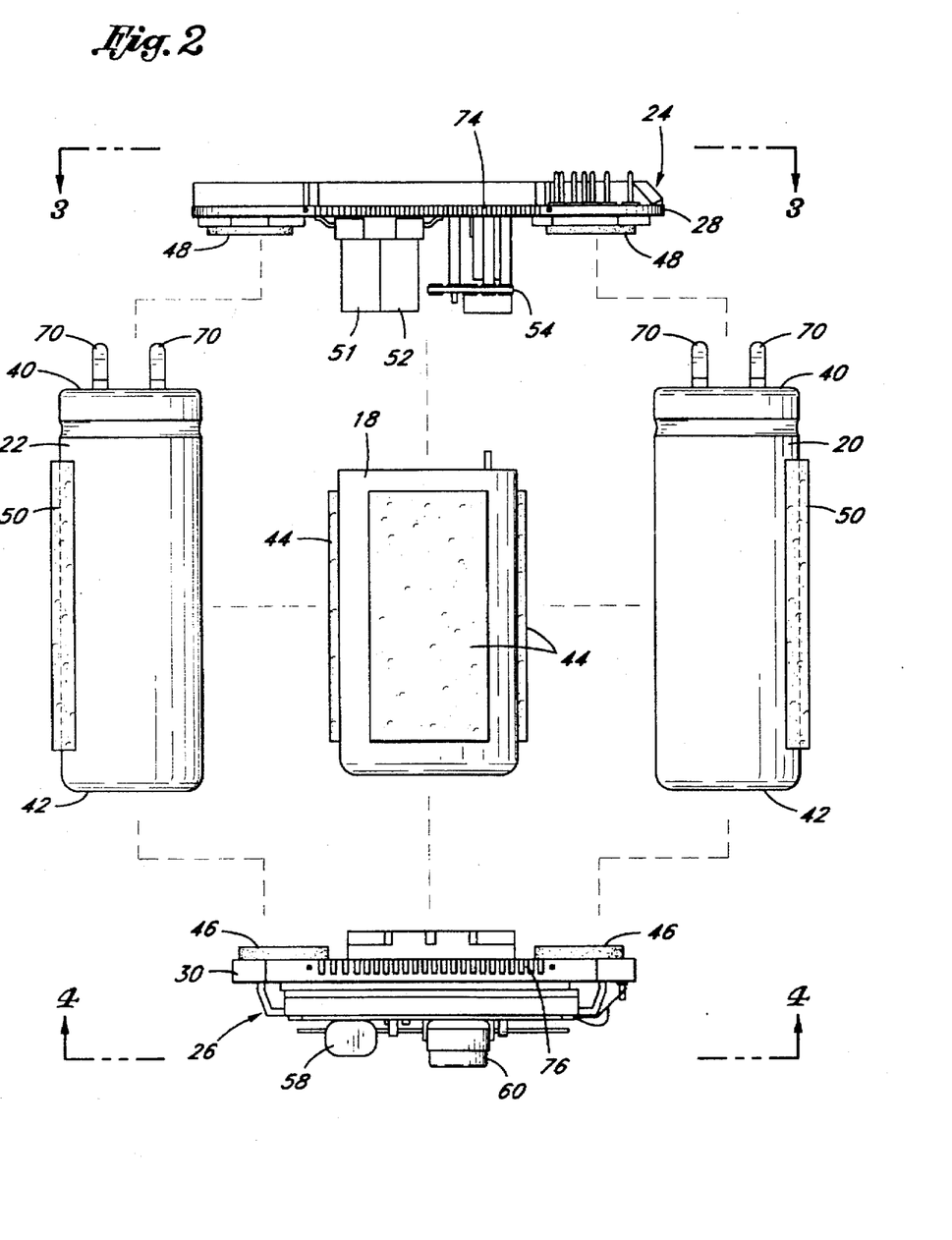
FIG. 2 is a plan view depicting the disassembled components of the device of FIG. 1.

Referring now to FIG. 2, the major internal components of the implantable device 10 are shown in a disassembled state. To further enhance volumetric efficiency, the capacitors 20 and 22, which must be in electrical communication with the high voltage module 24, are directly connected to the substrate 28. In accordance with a preferred embodiment, the interconnection architecture of the device 10 is simplified through this direct connection. Specifically, the capacitors 20 and 22 are shown with tabs 70 for direct insertion into or through slots 80 (shown in FIG. 3) formed within the substrate 28. Direct connection of the tabs 70 to the substrate 28 avoids the need for bulky flexible circuits or point-to-point wiring to establish electrical continuity, as found in the prior art.

With the arrangement of internal device components as described herein, consideration must be given to the structural integrity of the device under conditions of shock and vibration. Specifically, the relatively massive capacitors 20 and 22 are directly connected to form a rigid link with the relatively fragile electronics module 24. Undesirable stresses from this rigid link during movement must be avoided. Adequate protection against shock and vibration can be achieved by strengthening the module 24 and associated connections with the capacitors 20 and 22 and/or utilizing a secondary support structure to isolate the loads from these components.

In accordance with a preferred embodiment, a novel support structure comprising compressible adhesive foam is inserted between and around certain components of the stimulation device 10. As shown in FIG. 2, double-sided adhesive foam tape pieces 44 are attached to the battery 18 for contact upon assembly with the capacitors 20, 22, and the inside of the top container portion 16 (shown in FIG. 1). Adhesive foam pieces 46 are attached to the module 26 for contact with the bottom surfaces 42 of the capacitors 20 and 22. Similarly, adhesive foam pieces 48 are attached to the module 24 for contact with the top surfaces 40 of the capacitors 20 and 22. In addition, foam pieces 50 are placed around a section of the capacitors 20 and 22 for contact with the interior of the container 12. The advantages of using compressible foam as a support structure will be more fully explained in connection with FIG. 5.

Figure 3:
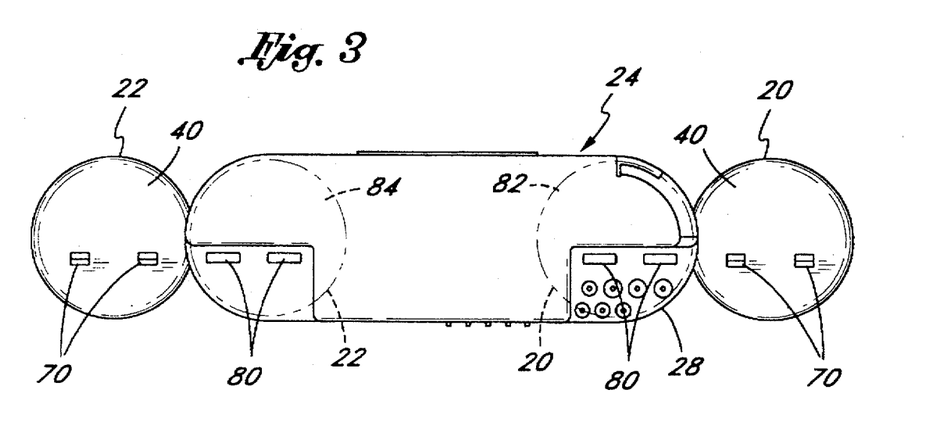
FIG. 3 is an elevation view of the stimulation device components shown in FIG. 2 taken along the line 3—3.

FIG. 3 depicts a top view of the components as seen along the line 3—3 of FIB. 2. The module 24 has four slots, or apertures 80, formed within the substrate 28 for receiving corresponding tabs 70 of the capacitors 20 and 22. In the assembled form, the capacitors 20 and 22 will be in the positions represented by the dashed lines 82 and 84, respectively.

Insertion of the capacitor tabs 70 through the slots 80 facilitates assembly of the device 10 because only a single solder or weld joint, or other means of connection, is required to secure each individual tab 70. Previous methods required two such connections for each tab 70 (one attaching the tab to a connector and a second from the connector to the substrate of the module). Directly connecting the capacitors 20 and 22 to the substrate 28 eliminates intermediary connections which can insert undesirable electrical resistance in the sensitive circuitry of the module 24. Direct connection results in a more reliable device because there are only half as many connections as would otherwise be required. Furthermore, insertion of the tabs 70 through the slots 80 promotes placement of the module 24 directly above the top surfaces 40 of the capacitors 20 and 22.

While FIG. 3 depicts a separate slot 80 for each capacitor tab 70, it can be appreciated that modifications to this arrangement can be made while maintaining the concept of inserting component electrical tabs directly through the substrate 28. For example, a longitudinal slot may be formed within the substrate 28 which receives both tabs from a given capacitor, each tab in turn connected to a different substrate contact. Even if cardioverter-defibrillators are designed to contain only a single capacitor, such a capacitor may have a tab or tabs directly inserted through a substrate module in accordance with the present invention. Similarly, other internal components, such as the battery, may be configured with tabs intended for direct insertion through a module substrate.

Figure 4:
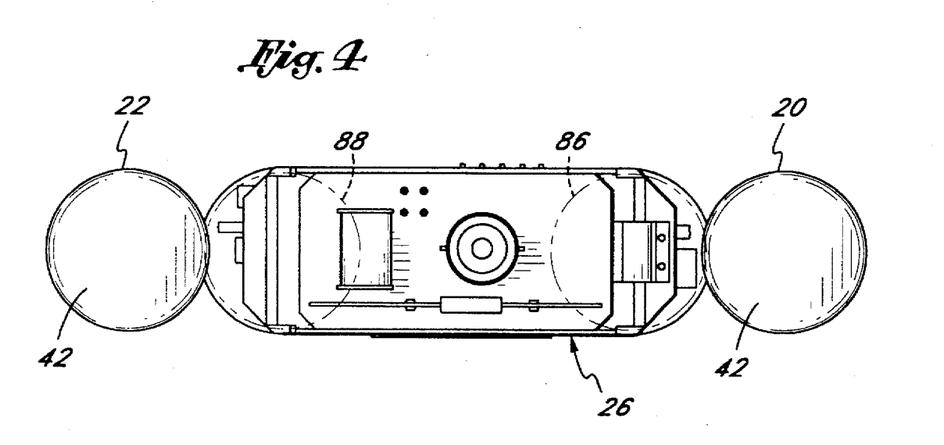
FIG. 4 is an elevation view of the stimulation device components shown in FIG. 2 taken along the line 4—4.

FIG. 4 depicts a top view of the components as seen along the line 4—4 of FIG. 2. As with the module 24, the control module 26 is oriented so that the generally planar configuration of the module 26 is perpendicular to the longitudinal axes of the capacitors 20 and 22. Accordingly, the surface of the substrate 30 is parallel with the bottom surfaces 42 of the capacitors 20, 22. In the assembled position, the bottom surfaces 42 lie above the module 26 in the positions represented by the dashed lines 86 and 88, respectively.

Figure 5:
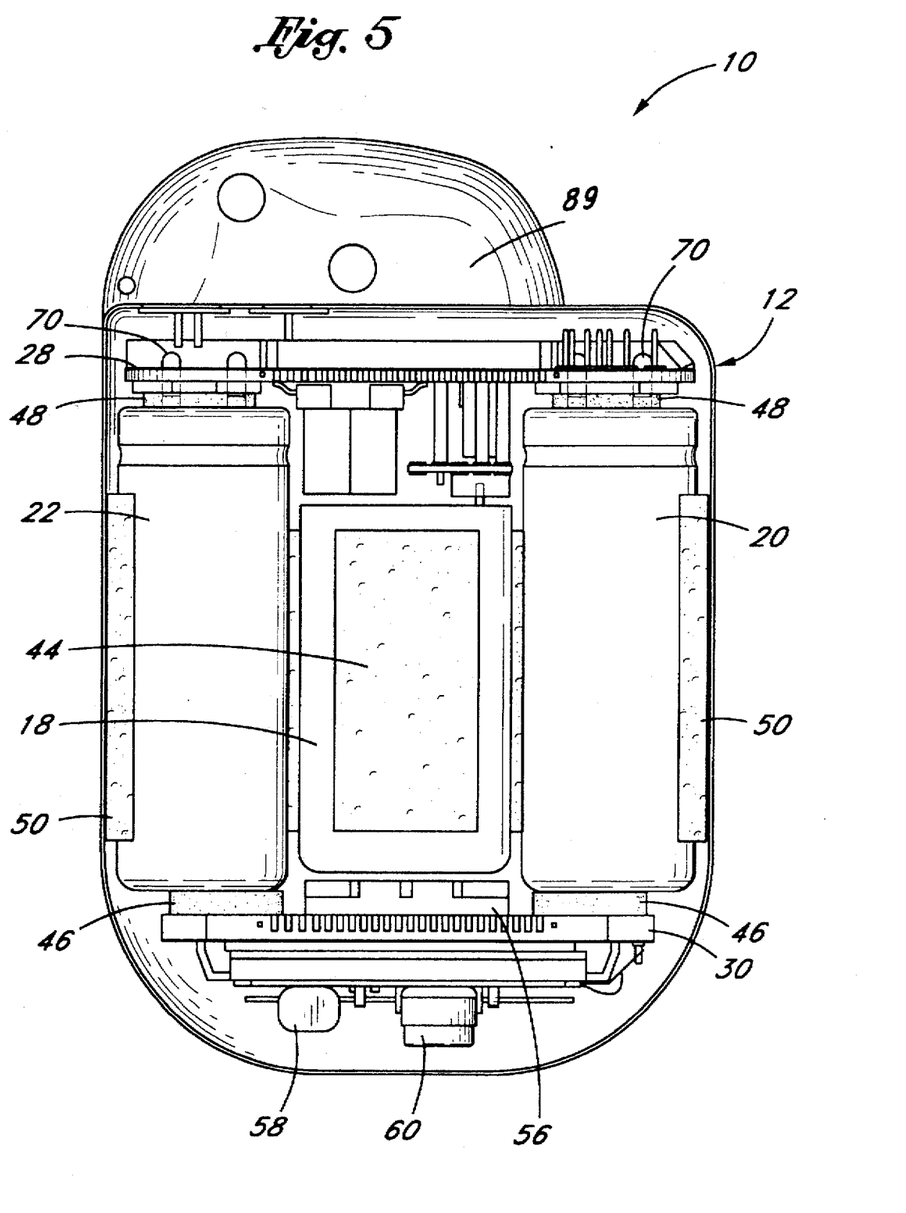
FIG. 5 is a plan view of a cardiac stimulation device depicting the configuration of the assembled internal components, and the interconnection of the capacitors and the high-voltage module, in accordance with a preferred embodiment.

Referring now to FIG. 5, an internal view of the stimulation device 10 is shown in final assembled form. The configuration of the internal components is advantageously optimized to reduce the required volume of the container 12. In particular, the modules 24 and 26 reside at opposite ends of the container 12 placed above and below the capacitors 20 and 22. Connection of the capacitors 20 and 22 to the high voltage module is facilitated by insertion of tabs 70 directly through the substrate 28. With the modules 24 and 26 positioned perpendicular to the longitudinal axes of the capacitors 20, 22, irregularly shaped components attached to the modules 24, 26, can advantageously extend inwardly to occupy regions surrounding the battery 18. Similarly, irregularly shaped components 58 and 60 extend outwardly toward the container to fill rounded voids at the periphery of the container 12.

FIG. 5 also depicts adhesive foam pieces 44, 46, 48, and 50 which serve to damp any shock or vibration of the device 10. As can be appreciated by one of ordinary skill in the art, additional foam pieces may be placed within the device 10 as needed to further secure the internal components from shock and vibration.

The adhesive foam pieces 44, 46, 48, and 50 may be standard double coated adhesive transfer tapes. The tape material must be compatible with the internal device components and in particular any coating material used on such components. For example, capacitors 20 and 22 may be covered with a protective poly-vinyl chloride (PVC) material. Tape products which are suitable for use in accordance with a preferred embodiment include the 3M brand Very High Bond Double Coated Acrylic Foam Tapes and Adhesive Transfer Tapes. The particular thickness of tape required will depend on the specific implantable device design, and on the tolerances encountered with a particular implantable unit from a given design.

Use of foam tape inserts to protect from shock and vibration offers distinct advantages from previous methods found in the prior art. For example, within different stimulation device units, internal components such as the battery 18 and the capacitors 20, 22, can have relatively large tolerance variations affecting overall rigidity. Through use of the slightly compressible adhesive foam pieces as described above, assembly of the pacemaker device 10 can accommodate variations in component tolerances without compromising overall rigidity and stability of the internal structure.

Traditional support structures used to guard against shock and vibration include skeletal plastic support elements which may have recesses for accommodating internal components. Although providing for adequate support in most cases, skeletal support structures must be specially designed and tooled leading to increased cost of the device 10. Lead times associated with manufacturing skeletal support structure tooling can be undesirable. Moreover, excessive tooling lead times can force the abandonment of certain design modifications occurring late in the stimulation device development cycle. Use of adhesive foam in the assembly process for the device 10 improves the speed at which the device reaches the manufacturing stage and provides considerable weight saving advantages over plastic support structures. It also provides the flexibility to adapt quickly to design changes to ensure adequate device stability.

Because the large capacitors 20 and 22 are directly connected to the relatively fragile module 24, movement of the capacitors 20 and 22 from shock or vibration must be shielded from the delicate module substrate 28, as well as surrounding components. Use of the compressible foam pieces 44, 46, and 48, provides effective shock damping because the entire internal subassembly of the device 10 is also attached to the container 12 through compressible foam pieces 50. Thus, shock loads are not directly transferred from the container 12 to the internal components through skeletal support structures. Also, because of the compressible nature of the foam pieces 44, 46, 48 and 50, minor damage to the container 12 will be less likely to cause damage to the delicate electronic components. All of these advantages can be achieved using a foam support structure which in most cases can be implemented less expensively than skeletal supports.

Although the foam support structure has been shown and described for a cardioverter-defibrillator in connection with FIG. 5, the same method is equally applicable to all implantable cardiac stimulation devices, e.g., pacemakers and the like.

Through the foregoing description and accompanying drawings, the present invention has been shown to have important advantages over current apparatus and methods for configuring the internal components of a cardiac stimulation device. The configuration of internal device components and corresponding component architecture has been shown to achieve unprecedented compactness and stability for an implantable cardiac stimulation device. While the above detailed description has shown, described, and pointed out the fundamental novel features of the invention, it will be understood that various omissions, substitutions and changes in the form and details of the device and methods illustrated may be made by those skilled in the art, without departing from the spirit of the invention. Therefore, the invention should be limited in its scope only by the following claims.

What is claimed is:

1. An implantable cardiac stimulation device having internal components optimally configured to reduce the overall volumetric displacement of the device comprising:

a container defining an interior region for holding an assembly of electronic components, the electronic components operating to deliver an electric shock to a patient in response to a cardiac arrhythmia, the assembly of electronic components comprising:

a voltage discharge module generating a high-voltage electric charge for delivering the electric shock to the patient, the voltage discharge module having an electrical substrate formed with an aperture therethrough;

a battery connected to the voltage discharge module for supplying electrical energy to generate the high-voltage electric charge; and a cardiac discharge capacitor assembly connected to the voltage discharge module for temporarily storing the high-voltage electric charge, the cardiac discharge capacitor assembly having an electrical connector lead directly inserted through the substrate aperture for establishing electrical communication with the voltage discharge module and achieving a reduced volumetric configuration for the stimulation device; and adhesive tape means for joining the voltage discharge module, the battery, and the capacitor assembly into a single, rigid assembly, thereby stabilizing the assembly against shock movement within the housing.

2. The cardiac stimulation device of claim 1, wherein the device is a cardioverter-defibrillator and the cardiac discharge capacitor assembly comprises first and second cylindrical capacitors, each of the first and second capacitors having a pair of electrical tabs formed at a first end of the first and second capacitors, and wherein each pair of electrical tabs is inserted through a respective mating aperture formed within the electrical substrate.

3. The cardiac stimulation device of claim 1, wherein:

the container is physiologically shaped comprising front and back substantially flat cover surfaces, and rounded peripheral edges for facilitating implantation;

the first and second capacitors are positioned at opposite edges of the interior region so that a longitudinal axis of the first capacitor is parallel to a longitudinal axis of the second capacitor;

the battery is positioned at a central portion of the interior region; and the adhesive means is applied between at least one of the container cover surfaces and at least one of the first capacitor, the second capacitor, or the battery, thereby stabilizing the single, rigid assembly to the container.

4. The cardiac stimulation device of claim 3, wherein the electrical substrate of the voltage discharge module has a substantially planar surface oriented perpendicular to the flat cover surfaces of the container.

5. The cardiac stimulation device of claim 4, wherein the voltage discharge module comprises electrical components mounted to the substrate of the voltage discharge module, and wherein the electrical components extend away from the planar surface of the substrate towards the battery to achieve an optimal reduced volumetric configuration.

6. The cardiac stimulation device of claim 3, wherein the cardioverter-defibrillator further comprises a control module for monitoring cardiac functions of the patient and communicating with the voltage discharge module, the control module positioned at a second end of the first and second capacitors, and the control module comprising a substantially planar substrate surface oriented perpendicular to the flat cover surfaces of the container.

7. The cardiac stimulation device of claim 6, wherein the control module comprises a first electronic component mounted to a top surface of the control module substrate, and a second electronic component mounted to a bottom surface of the control module substrate, the first electronic component extending away from the top surface towards the battery and the second electronic component extending away from the bottom surface towards an edge of the container.

8. The cardiac stimulation device of claim 1, wherein the adhesive means comprises adhesive foam tape placed between the cardiac discharge capacitor assembly and the voltage discharge module, between the cardiac discharge capacitor assembly and the battery, and between the cardiac discharge capacitor assembly and the container for providing stabilization of the assembly of internal components in response to movement of the cardiac stimulation device.

9. An implantable cardioverter-defibrillator comprising:

a container constructed of a biocompatible material for subcutaneous positioning within a human patient;

electronic circuit means disposed within an interior region of the container for monitoring the cardiac activity of a patient and delivering a high voltage charge to the patient in response to a cardiac arrhythmia;

a battery within the interior region of the container for supplying electrical energy to the electronic circuit means; and energy storage means disposed within the interior region of the container for storing the high voltage electrical charge, the energy storage means comprising electrical connection means for transferring the high voltage charge to the electronic circuit means;

compressible tape adhesive means for protecting the energy storage means and the electronic circuit means against shock and vibration; and wherein the electronic circuit means is formed with at least one aperture for receiving the electrical connection means of the energy storage means.

10. The implantable cardioverter-defibrillator of claim 9, wherein the container comprises flat cover surfaces terminating at a plurality of edges about a periphery, the energy storage means comprising a pair of high-voltage capacitors positioned at opposite edges of the container within the interior region, the electronic circuit means comprising a first module having a substantially planar substrate formed with the at least one aperture, and wherein the substantially planar substrate is placed perpendicular to the flat cover surfaces of the container.

11. The implantable cardioverter-defibrillator of claim 10, wherein the high-voltage capacitors are cylindrically shaped and the electrical connection means is a pair of contact tabs formed on a flat top surface of each capacitor, the flat top surfaces of the capacitors positioned adjacent to the first module and the contact tabs directly inserted into the at least one aperture.

12. The implantable cardioverter-defibrillator of claim 10, wherein the electronic circuit means further comprises a second module for performing cardiac monitoring functions of the patient, the second module having a substantially planar substrate with individual circuit components mounted thereon, and wherein the substantially planar substrate of the second module is placed perpendicular to the flat cover surfaces of the container.

13. The implantable cardioverter-defibrillator of claim 12, wherein the high-voltage capacitors each comprise a flat bottom surface positioned in substantially the same plane and wherein the second module is placed adjacent to the flat bottom surfaces of the capacitors.

14. The implantable cardioverter-defibrillator of claim 9, wherein the compressible adhesive means comprises adhesive foam sections for damping the physical shock and vibration placed between (1) the energy storage means and the electronic circuit means; (2) between the energy storage means and the container; and (3) between the energy storage means and the battery.

15. An implantable cardioverter-defibrillator having a reduced volumetric displacement comprising:

a container constructed of a biocompatible material for subcutaneous positioning within a human patient, the container formed with substantially planar top and bottom surfaces merging at a rounded periphery;

a battery housed at a substantially central region within the container for providing electrical power to the cardioverter-defibrillator;

first energy storage means housed within the container for storing a high voltage electric charge, the first energy storage means in electrical communication with the battery and positioned at a first edge of the rounded periphery;

second energy storage means housed within the container for storing a high voltage electric charge, the second energy storage means in electrical communication with the battery and positioned at a second edge of the rounded periphery opposite the first edge;

electronic circuit means housed within the container for monitoring and regulating cardiac activity of the patient, the electronic circuit means attached to the first and second energy storage means for delivering the high voltage electric charge to the patient in response to a cardiac arrhythmia;

wherein the electronic circuit means comprises (1) a first circuit module having a first substantially planar substrate and individual circuit components mounted thereon, the first planar substrate positioned perpendicular to the planar top and bottom surfaces of the container at a third edge of the rounded periphery, and (2) a second circuit module having a second substantially planar substrate for mounting electrical components thereto, the second planar substrate of the second circuit module positioned perpendicular to the planar top and bottom surfaces of the container at a fourth edge of the rounded periphery;

compressible tape adhesive means for protecting the electronic circuit means and the first and second energy storage means against shock and vibration.

16. The implantable cardioverter-defibrillator of claim 15, wherein the first and second energy storage means each comprise a high-voltage capacitor having electrical contact means attached to a respective top surface of the high-voltage capacitors, the first circuit module of the electronic circuit means having a first aperture formed thereon for receiving the electrical contact means of the first energy storage device and a second aperture formed thereon for receiving the electrical contact means of the second energy storage device.

17. The implantable cardioverter-defibrillator of claim 15, wherein the first and second energy storage means comprise electrical contact means inserted through the first planar substrate for establishing a direct electrical connection to the first circuit module.

18. The implantable cardioverter-defibrillator of claim 15, wherein individual circuit components are mounted to the second substrate of the second circuit module, the individual circuit components extending away from the second substrate towards the fourth edge of the rounded periphery.

19. The implantable cardioverter-defibrillator of claim 15, further comprising compressible support means for protecting the implantable cardioverter-defibrillator against physical shock and vibration, the compressible support means comprising adhesive foam pieces for damping the physical shock and vibration, wherein the adhesive foam pieces are placed between (1) the electronic circuit means and first energy storage means; (2) the electronic circuit means and second energy storage means; (3) the first energy storage means and the first edge of the container; and (4) the second energy storage means and the second edge of the container.

20. An implantable cardiac stimulation device for subcutaneous positioning within a human patient comprising:

a container defining an interior region for housing electrical components of the stimulation device;

a battery housed within the container for providing electrical power to the stimulation device;

energy storage means housed within the container for storing an electric charge received from the battery;

electronic circuit means housed within the container for monitoring and regulating cardiac activity of the patient, the electronic circuit means connected to the battery and energy storage means and delivering electric pulses to the patient in response to detected cardiac activity of the patient; and compressible tape support means positioned within the container for providing stabilization of the energy storage means and electronic circuit means in response to movement of the cardiac stimulation device, the compressible tape support means positioned between the electronic circuit means and the energy storage means, and the compressible support means positioned between the energy storage means and an interior surface of the container.

21. The implantable cardiac stimulation device of claim 20, wherein the stimulation device is a pacemaker for monitoring the heartbeat of the patient and providing an electronic stimulus to the heart of the patient to regulate the heartbeat.

22. The implantable cardiac stimulation device of claim 20 wherein the compressible support means comprises adhesive foam.

23. The implantable cardiac stimulation device of claim 22, wherein the adhesive foam is a double-sided adhesive acrylic tape.

24. The implantable cardiac stimulation device of claim 20, wherein the stimulation device is a defibrillator and the energy storage means comprises a pair of high voltage discharge capacitors.

25. The implantable cardiac stimulation device of claim 24, wherein the container comprises flat cover surfaces terminating at a plurality of edges about a periphery, the pair of high-voltage capacitors positioned at opposite edges of the container within the interior region, the electronic circuit means comprising a first module having a substantially planar substrate formed with a plurality of apertures for receiving electrical leads attached to the pair of high-voltage capacitors, and wherein the substantially planar substrate is placed perpendicular to the flat cover surfaces of the container.

26. A method of constructing an implantable cardioverter-defibrillator to achieve a reduced volumetric displacement wherein the cardioverter-defibrillator comprises a container having substantially planar top and bottom covering surfaces for housing a battery, a cylindrical charge capacitor having electrical contact tabs, and an electronic module having a substantially planar substrate surface, all for delivering a high-voltage charge to a patient, the method of constructing comprising the following steps:

forming at least one opening within the electronic module for receiving at least one of the electrical contact tabs of the charge capacitor;

inserting the at least one electrical contact tab into the at least one opening formed within the electronic module;

securing the at least one electrical contact tab to the electronic module to establish electrical connection between the electronic module and the charge capacitor;

placing the charge capacitor and electronic module combination within the container so that the longitudinal axis of the capacitor is parallel to the planar top and bottom surfaces of the container and so that the planar substrate surface of the electronic module is perpendicular to the planar top and bottom surfaces of the container;

attaching a first piece of compressible tape adhesive material to the electronic module wherein the first piece of adhesive material is secured between the electronic module and the charge capacitor to damp movement of the charge capacitor relative to movement of the electronic module; and attaching a second piece of compressible tape adhesive material to the charge capacitor wherein the second piece of adhesive material as secured between the charge capacitor and an interior surface of the container to damp movement of the charge capacitor relative to movement of the container.

27. The method of claim 26, wherein the step of securing comprises the step of soldering the at least one electrical contact tab to the electronic module.

28. The method of claim 26, wherein the implantable cardioverter-defibrillator further comprises a second charge capacitor having a pair of electrical contact tabs, the method of constructing an implantable cardioverter-defibrillator further comprising the step of inserting the electrical contact tabs of the second charge capacitor through the at least one opening formed in the electronic module.

29. The method of claim 26 wherein the first and second pieces of compressible adhesive material are tape.

30. A method of constructing an implantable cardiac stimulation device to achieve a high degree of stabilization and protection from shock and vibration wherein the cardiac stimulation device comprises a container for housing a battery, a capacitor placed within the container for discharging an electrical stimulus delivered to a host patient, and an electrical control module connected to the capacitor and to the battery for monitoring the cardiac activity of a patient and delivering the electrical stimulus in response to irregular cardiac activity of the patient, the method of constructing comprising the following steps:

securing a first section of compressible adhesive tape between the electrical control module and the capacitor to damp movement of the capacitor relative to the electrical control module;

securing a second section of compressible adhesive tape between the capacitor and an interior surface of the container to damp movement of the capacitor relative to the container; and securing a third section of compressible adhesive tape between the capacitor and the battery to damp movement of the capacitor relative to the battery.

31. The method of claim 30, wherein the device is a cardioverter-defibrillator and the capacitor is a high voltage discharge capacitor having contact tabs directly connected to the electrical control module.

32. The method of claim 31, further comprising the additional step of attaching a fourth section of adhesive tape between the battery and the interior surface of the container to damp movement of the battery relative to the container.

33. An implantable cardiac stimulation device having internal components optimally configured to reduce the overall volumetric displacement of the device comprising:

a hermetically-sealed, physiologically-shaped housing for holding a single, rigid sub-assembly of electronic components, the electronic components including means for delivering an electric shock to a patient in response to a cardiac arrhythmia, the rigid sub-assembly of electronic components comprising:

a non-hermetic electronic module generating a high-voltage electric charge for delivering the electric shock to the patient, the electronic module having an electrical substrate formed with apertures therethrough;

a pair of capacitors, connected to the electronic module, for temporarily storing the high-voltage electric charge, each capacitor having terminals which are directly inserted through the substrate apertures for establishing electrical communication with the electronic module;

a battery, electrically connected to the electronic module, located at a substantially central region between the pair of capacitors for supplying electrical energy to generate the high-voltage electric charge; and adhesive means for joining the non-hermetic electronic tape module, the battery, and the pair of capacitors into a single, rigid sub-assembly, thereby stabilizing the sub-assembly against shock movement within the housing and achieving a reduced volumetric configuration for the stimulation device.

34. The cardiac stimulation device of claim 33, wherein:

the adhesive means is applied between the housing and at least one of the pair of capacitors and the battery, thereby stabilizing the single, rigid assembly to the housing.

* * * * *